(12) United States Patent
Bolli et al.

(10) Patent No.: US 7,868,012 B2
(45) Date of Patent: Jan. 11, 2011

(54) SULFAMIDES AS ENDOTHELIN RECEPTOR ANTAGONISTS FOR THE TREATMENT OF CARDIOVASCULAR DISEASES

(75) Inventors: Martin Bolli, Allschwil (CH); Christoph Boss, Allschwil (CH); Martine Clozel, Binningen (CH); Walter Fischli, Allschwil (CH); Thomas Weller, Binningen (CH)

(73) Assignee: Actelion Pharmaceuticals, Ltd., Allschwil (CH)

( * ) Notice: Subject to any disclaimer, the term of this patent is extended or adjusted under 35 U.S.C. 154(b) by 877 days.

(21) Appl. No.: 11/718,922

(22) PCT Filed: Nov. 11, 2005

(86) PCT No.: PCT/IB2005/053716

§ 371 (c)(1), (2), (4) Date: May 9, 2007

(87) PCT Pub. No.: WO2006/051502

PCT Pub. Date: May 18, 2006

(65) Prior Publication Data

US 2008/0004298 A1 Jan. 3, 2008

(30) Foreign Application Priority Data

Nov. 11, 2004 (WO) ................ PCT/EP2004/012774

(51) Int. Cl.
C07D 403/12 (2006.01)
A61K 31/506 (2006.01)
(52) U.S. Cl. ........................................ 514/269; 544/296
(58) Field of Classification Search ................. 544/296; 514/269
See application file for complete search history.

(56) References Cited

FOREIGN PATENT DOCUMENTS

| EP | 0 526 708 A1 | 2/1993 |
|---|---|---|
| EP | 0 743 307 A1 | 11/1996 |
| EP | 0 658 548 B1 | 11/1997 |
| EP | 0 882 719 A1 | 12/1998 |
| EP | 0 633 259 B1 | 1/1999 |
| EP | 0 959 072 A1 | 11/1999 |
| WO | WO-96/19459 A1 | 6/1996 |
| WO | WO-02/053557 A | 7/2002 |
| WO | WO-2004/050640 A | 6/2004 |

OTHER PUBLICATIONS

Simone, Oncology: Introduction, Cecil Textbook of Medicine, 20th Edition, vol. 1, pp. 1004-1010, 1996.*
Morimoto, H., et al.; "Potent and Selective ET-A Antagonists. 2. Discovery and Evaluation of Potent and Water Soluble N-(6-(2-(Aryloxy)ethoxy)-4-pyrimidinyl)sulfonamide Derivatives"; J. Med. Chem. 2001, vol. 44, pp. 3369-3377.
Yanagisawa, M., et al.; "A novel potent vasoconstrictor peptide produced by vascular endothelial cells"; Nature, vol. 332, Mar. 1988, pp. 411-415.
McMillen, M. et al.; "Endothelins: Polyfunctional Cytokines"; Journal of the American College of Surgeons, vol. 180, May 1995, pp. 621-637.
Rubanyi, G.M. et al.; "Endothelins: Molecular Biology, Biochemistry, Pharmacology, Physiology, and Pathophysiology"; Pharmacological Reviews, vol. 46, No. 3, 1994, pp. 328-415.
Arai, H. et al.; "Cloning and expression of a cDNA encoding and endothelin receptor"; Nature, vol. 348, 1990, pp. 730-732.
Sakurai, T. et al.; "Cloning of a cDNA encoding a non-isopeptide-selective subtype of the endothelin receptor"; Nature, vol. 348, 1990, pp. 732-735.
Ohlstein E. H. et al.; "Endothelin-1 Modulates Vascular Smooth Muscle Structure and Vasomotion: Implications in Cardiovascular Pathology"; Drug Development Research, vol. 29, 1993, pp. 108-128.
Ogawa, Y. et al.; "Molecular Cloning of a Non-Isopeptide-Selective Human Endothelin Recpetor"; Biochemical and Biophysical Research Communications, vol. 178, No. 1, 1991, pp. 248-255.
Sumner, M. et al.; "Endothelin $ET_A$ and $ET_B$ receptors mediate vascular smooth muscle contraction"; Br. J. Pharmacol, vol. 107, 1992, pp. 858-860.
Breu, V. et al.; "In vitro characterization of Ro 46-2005, a novel synthetic non-peptide endothelin antagonist of $ET_A$ and $ET_B$ receptors"; FEBS Letters, vol. 334, No. 2, 1993, pp. 210-214.
Neidhart, W. et al.; "The Discovery of Nonpeptide Endothelin Receptor Antagonists. Progression towards Bosentan"; Chimia, vol. 50, 1996, pp. 519-524.
Neidhart, W. et al.; "Discovery of RO 48-5695: A Potent Mixed Endothelin Receptor Antagonist Optimized From Bosentan"; Bioorganic & Medicinal Chemistry Letters, vol. 7, No. 17, 1997, pp. 2223-2228.
Nugent, R. et al.; "Pyrimidine Thioethers: A Novel Class of HIV-1 Reverse Transcriptase Inhibitors with Activity Against BHAP-Resistant HIV"; Journal of Medicinal Chemistry., vol. 41, 1998, pp. 3793-3803.
Crosby, D. et al.; "n—Butyl 5-Choloro-2-pyrimidoxyacetate—A Plant Growth Regulator Analog"; J. Med. Chem. Soc., vol. 25, 1960, pp. 1916-1919.
Brown, D.J. et al.; "Pyrimidine Reactions"; Aus. J. Chem, vol. 17, 1964, pp. 794-802.
Paquette, L. et al; "The Chlorination of Conjugated Dienamides. A New Application of the Principles of Least Motion"; J. Org. Chem., vol. 32, 1967, pp. 2725-2731.
Tozer, M. et al.; "4-Chlorobenzyl Sulfonamide and Sulfamide Derivatives of Histamine Homologues: The Design of Potent Histamine $H_3$ Receptor Antagonists"; Bioorganic & Medicinal Chemistry Letters, vol. 9, 1999, pp. 3103-3108.
Dewynter, G. et al.; "Synthese de "sulfahydantoines" chirales. Aspects stereochimiques et protection regiospecifique"; Tetrahedron, vol. 49, No. 1, 1993, pp. 65-76.

* cited by examiner

*Primary Examiner*—Deepak Rao
(74) *Attorney, Agent, or Firm*—Hoxie & Associates LLC

(57) ABSTRACT

The invention relates to novel sulfamic acid amides and their use as active ingredients in the preparation of pharmaceutical compositions. The invention also concerns related aspects including pharmaceutical compositions containing one or more of those compounds and especially their use as endothelin receptor antagonists.

13 Claims, No Drawings

SULFAMIDES AS ENDOTHELIN RECEPTOR ANTAGONISTS FOR THE TREATMENT OF CARDIOVASCULAR DISEASES

This application is a U.S. filing under 35 U.S.C. 371 of PCT/IB05/53716, filed on Nov. 11, 2005, which claims the benefit of PCT/EP2004/012774, filed on Nov. 11, 2004, the disclosures of each of which are incorporated herein by reference. The present invention relates to novel pyrimidine-sulfamides of formula I and their use as active ingredients in the preparation of pharmaceutical compositions. The invention also concerns related aspects including processes for the preparation of the compounds, pharmaceutical compositions containing one or more compounds of Formula I, and especially their use as endothelin receptor antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al.: J Am Coll Surg (1995) 180:621). They participate in bronchoconstriction and regulate neurotransmitter release, activation of inflammatory cells, fibrosis, cell proliferation and cell differentiation (Rubanyi G M et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the three endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, pulmonary hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, only one endothelin receptor antagonist (Tracleer™) is marketed and several are in clinical trials. However, some of these molecules possess a number of weaknesses such as complex synthesis, low solubility, high molecular weight, poor pharmacokinetics, or safety problems (e.g. liver enzyme increases). Furthermore, the contribution of differing $ET_A/ET_B$ receptor blockade to the clinical outcome is not known. Thus, tailoring of the physicochemical and pharmacokinetic properties and the selectivity profile of each antagonist for a given clinical indication is mandatory. In previous patent applications we disclosed endothelin receptor antagonists with a pyrimidine core structure containing a sulfamide unit [WO 02/0533557 A1; WO 04/050640]. We have discovered a new class of substituted pyrimidines of the structure below and found that they allow the specific tailoring described above. In particular, the compounds of the present invention exhibit a greater water solubility by at least one order of magnitude over a wide pH range when compared to the compounds disclosed in WO 02/0533557 A1 and WO 04/050640.

The inhibitory activity of the compounds of general formula I on endothelin receptors can be demonstrated using the test procedures described hereinafter: For the evaluation of the potency and efficacy of the compounds of the general formula I the following tests were used:

1) Inhibition of Endothelin Binding to Membranes from CHO Cells Carrying Human ET Receptors:

For competition binding studies, membranes of CHO cells expressing human recombinant $ET_A$ or $ET_B$ receptors were used. Microsomal membranes from recombinant CHO cells were prepared and the binding assay made as previously described (Breu V., et al, FEBS Lett 1993; 334:210).

The assay is performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabeled antagonists. Maximum and minimum binding were estimated in samples without and with 100 nM ET-1, respectively. After 2 h, the membranes were filtered on filterplates containing GF/C filters (Unifilterplates from Canberra Packard S. A. Zürich, Switzerland). To each well, 50 uL of scintillation cocktail is added (MicroScint 20, Canberra Packard S. A. Zürich, Switzerland) and the filter plates counted in a microplate counter (TopCount, Canberra Packard S. A. Zürich, Switzerland).

All the test compounds were dissolved, diluted and added in DMSO. The assay is run in the presence of 2.5% DMSO which is found not to interfere significantly with the binding. $IC_{50}$ is calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of General Formula I are given in Table 1.

TABLE 1

| Compound of Example | $IC_{50}$[nM] | |
| --- | --- | --- |
| | $ET_A$ | $ET_B$ |
| Example 1 | 0.603 | 322 |
| Example 2 | 0.656 | 330 |

2) Inhibition of Endothelin-Induced Contractions on Isolated Rat Aortic Rings ($ET_A$ Receptors) and Rat Tracheal Rings ($ET_B$ Receptors):

The functional inhibitory potency of the endothelin antagonists was assessed by their inhibition of the contraction induced by endothelin-1 on rat aortic rings ($ET_A$ receptors) and of the contraction induced by sarafotoxin S6c on rat tracheal rings ($ET_B$ receptors). Adult Wistar rats were anesthetized and exsanguinated. The thoracic aorta or trachea were excised, dissected and cut in 3-5 mm rings. The endothelium/epithelium was removed by gentle rubbing of the intimal surface. Each ring was suspended in a 10 mL isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° C. and gassed with 95% O$_2$ and 5% CO$_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the EC$_{50}$ induced by different concentrations of test compound. EC$_{50}$ is the concentration of endothelin needed to get a half-maximal contraction, pA$_2$ is the negative logarithm of the antagonist concentration which induces a two-fold shift in the EC$_{50}$ value.

The pA$_2$ values obtained with compounds of formula I are given in Table 2.

TABLE 2

| Compound of Example | pA$_2$ value | |
| --- | --- | --- |
|  | Aorta | Trachea |
| Example 1 | 7.0 | 5.5 |
| Example 2 | 8.2 | 6.1 |

Because of their ability to inhibit the endothelin binding, the described compounds can be used for treatment of diseases, which are associated with an increase in vasoconstriction, proliferation or inflammation due to endothelin. Examples of such diseases are hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome, digital ulcers and portal hypertension. They can also be used in the treatment or prevention of atherosclerosis, restenosis after balloon or stent angioplasty, inflammation, stomach and duodenal ulcer, cancer, melanoma, prostate cancer, prostatic hypertrophy, erectile dysfunction, hearing loss, amaurosis, chronic bronchitis, asthma, pulmonary fibrosis, gram negative septicemia, shock, sickle cell anemia, glomerulonephritis, renal colic, glaucoma, connective tissue diseases, therapy and prophylaxis of diabetic complications, complications of vascular or cardiac surgery or after organ transplantation, complications of cyclosporin treatment, pain, hyperlipidemia as well as other diseases, presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1-50 mg/kg body weight per day are considered. The preparations with compounds can contain inert or as well pharmacodynamically active excipients. Tablets or granules, for example, could contain a number of binding agents, filling excipients, carrier substances or diluents.

The present invention relates to pyrimidine-sulfamides of the General Formula I,

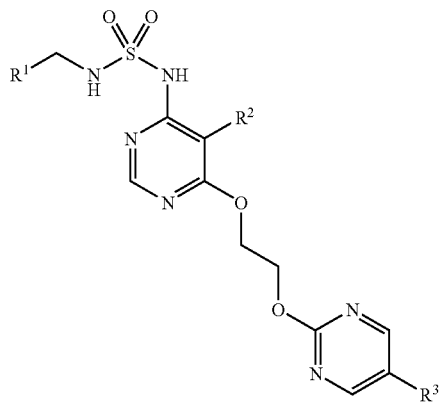

General Formula (I)

wherein
R$^1$ represents —CH(OH)—CH$_3$, —CH$_2$—CH$_2$OH, —CH$_2$COOH, —CH$_2$—CH$_2$—CH$_2$OH, —CH$_2$—CH$_2$—COOH;

R$^2$ represents 4-bromophenyl, 4-chlorophenyl, 4-methylphenyl, 2-methoxyphenoxy, 3-methoxyphenoxy, 2-chloro-5-methoxy-phenoxy;

R$^3$ represents bromine or chlorine;

and optically pure enantiomers, mixtures of enantiomers such as racemates, and pharmaceutically acceptable salts thereof.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide and the like.

The compounds of the general formula I might have one asymmetric carbon atom and may be prepared in form of optically pure enantiomers, mixtures of enantiomers, and racemates. The present invention encompasses all these forms. Mixtures may be separated in a manner known per se, i.e. by column chromatography, thin layer chromatography, HPLC or crystallization.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension, and pulmonary hypertension. They can also be used for the treatment or prevention of atherosclerosis, restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, hyperlipidemia as well as other diseases presently known to be related to endothelin.

These compositions may be administered in enteral or oral form e.g. as tablets, dragees, gelatine capsules, emulsions, solutions or suspensions, in nasal form like sprays or rectally in form of suppositories. These compounds may also be administered intramuscularly, parenterally or intraveneously, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols may be used. For the preparation of solutions and sirups e.g. water, polyols, saccharose, glucose can be used. Injectables can be prepared by using e.g. water, polyols, alcohols, glycerin, vegetable oils, lecithin, or liposomes. Suppositories may be prepared by using natural or hydrogenated oils, waxes, fatty acids (fats), liquid or half-liquid polyols.

The compositions may contain in addition preservatives, stability improving substances, viscosity improving or regulating substances, solubility improving substances, sweeteners, dyes, taste improving compounds, salts to change the osmotic pressure, buffer or anti-oxidants.

The compounds of general formula I may also be used in combination with one or more other therapeutically useful substances e.g. α- and β-blockers like phentolamine, phenoxybenzamine, atenolol, propranolol, timolol, metoprolol, carteolol and the like; vasodilators like hydralazine, minoxidil, diazoxide, or flosequinan; calcium-antagonists like diltiazem, nicardipine, nimodipine, verapamil or nifedipine; ACE-inhibitors like cilazapril, captopril, enalapril, lisinopril and the like; potassium channel activators like pinacidil; angiotensin II receptor antagonists like losartan, valsartan, irbesartan and the like; diuretics like hydrochiorothiazide, chlorothiazide, acetolamide, bumetanide, furosemide, metolazone or chlortalidone; sympatholitics like methyldopa, clonidine, guanabenz, or reserpine; prostacyclin derivatives like flolan; anti-cholinergic substances and other therapeutics which serve to treat high blood pressure or any cardiac disorders.

The dosage may vary within wide limits but should be adapted to the specific situation. In general the dosage given daily in oral form should be between about 1 mg and about 1 g, preferably between about 3 mg and about 500 mg, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

In a preferred embodiment of the invention, $R^1$ represents —$CH_2$—$CH_2OH$ and $R^2$ and $R^3$ are as defined in General Formula (I) above;

and optically pure enantiomers, mixtures of enantiomers such as racemates, and pharmaceutically acceptable salts thereof.

In another preferred embodiment of the invention, $R^1$ represents —$CH_2$—COOH and $R^2$ and $R^3$ are as defined in General Formula (I) above;

and optically pure enantiomers, mixtures of enantiomers such as racemates, and pharmaceutically acceptable salts thereof.

In yet another preferred embodiment of the invention $R^2$ represents 4-bromophenyl, and $R^1$ and $R^3$ are as defined in General Formula (I) above;

and optically pure enantiomers, mixtures of enantiomers such as racemates, and pharmaceutically acceptable salts thereof.

In a further preferred embodiment of the invention $R^3$ represents bromine, and $R^1$ and $R^2$ are as defined in General Formula (I) above;

and optically pure enantiomers, mixtures of enantiomers such as racemates, and pharmaceutically acceptable salts thereof.

In a particularly preferred embodiment of the invention, $R^1$ represents —$CH_2$—$CH_2OH$ or —$CH_2$—COOH, $R^2$ represents phenyl, substituted in 4-position by halogen, and $R^3$ is defined as in General Formula (I) above;

and optically pure enantiomers, mixtures of enantiomers such as racemates, and pharmaceutically acceptable salts thereof.

In a further particularly preferred embodiment of the invention, $R^1$ represents —$CH_2$—$CH_2OH$, $R^2$ represents 4-bromophenyl, and $R^3$ is defined as in General Formula (I) above;

and optically pure enantiomers, mixtures of enantiomers such as racemates, and pharmaceutically acceptable salts thereof.

In another particularly preferred embodiment of the invention, $R^1$ represents —$CH_2$—COOH, $R^2$ represents 4-bromophenyl, and $R^3$ is defined as in General Formula (I) above;

and optically pure enantiomers, mixtures of enantiomers such as racemates, and pharmaceutically acceptable salts thereof.

Particularly preferred compounds are:
3-hydroxypropylsulfamic acid{5-(4-bromophenyl)-6-[2-(5-bromopyrimidin-2-yloxy)-ethoxy]-pyrimidin-4-yl}-amide,
2-hydroxycarbonylethylsulfamic acid{5-(4-bromophenyl)-6 [2(5bromopyrimidin-2-yloxy)-ethoxy]-pyrimidin-4-yl}-amide.

Compounds of the General Formula (I) of the present invention can be prepared according to the general sequence of reactions outlined below. For simplicity and clarity reasons sometimes only parts of the synthetic possibilities which lead to compounds of General Formula (I) are described.

Possibility A:

The desired compounds of General Formula I can be prepared by reacting a compound of the Formula 1:

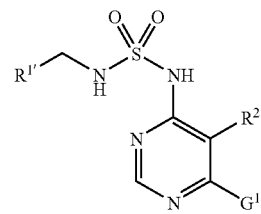

Formula 1 wherein $G^1$ is a reactive residue, preferentially a chlorine atom, with a compound of the Formula 2,

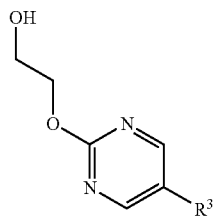

Formula 2 wherein $R^3$ is as defined in General Formula (I) above, or a salt thereof. In Formula 1 the symbol $R^{1'}$ may be as defined for $R^1$ in General Formula (I), or preferentially represents a suitably protected precursor of the residue $R^1$. In this latter case, deprotection is required as a last step to generate the compounds of General Formula (I). $R^2$ is as defined in General Formula (I).

Formula 3

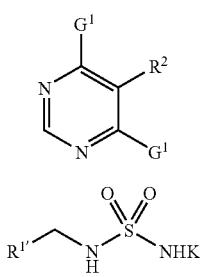

Formula 4

R$^{1'}$ CH$_2$ N(H) S(O)$_2$ NHK

The compounds of Formula 1 can be prepared by reacting a compound of Formula 3 with a compound of Formula 4 in the presence or absence of an additional base in solvents such as DMF, DMSO, THF or mixtures thereof. The preparation of compounds of Formula 3 may follow literature procedures (e.g. W. Neidhart, V. Breu, D. Bur, K. Burri, M. Clozel, G. Hirth, M. Müller, H. P. Wessel, H. Ramuz; *Chimia*, 1996, 50, 519-524 and references cited there; W. Neidhart, V. Breu, K. Burri, M. Clozel, G. Hirth, U. Klinkhammer, T. Giller, H. Ramuz; *Bioorg. Med. Chem. Lett.*, 1997, 7, 2223-2228. R. A. Nugent, S. T. Schlachter, M. J. Murphy, G. J. Cleek, T. J. Poel, D. G. Whishka, D. R. Graber, Y. Yagi, B. J. Keiser, R. A. Olmsted, L. A. Kopta, S. M. Swaney, S. M. Poppe, J. Morris, W. G. Tarpley, R. C. Thomas; *J. Med. Chem.*, 1998, 41, 3793-3803.). The preparation of compounds of Formula 4 is outlined below.

Possibility B:

The compounds of General Formula (I) may also be prepared by reacting a compound of Formula 5

Formula 5

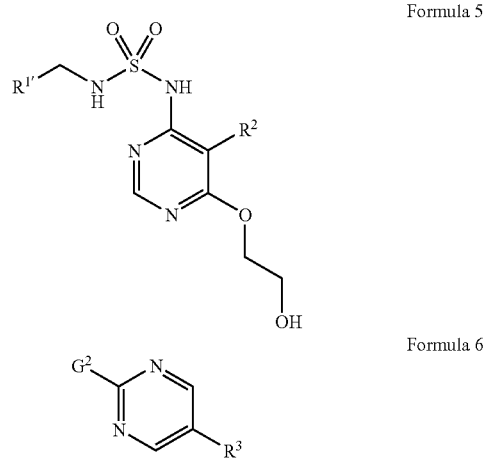

Formula 6 with a compound of the Formula 6, wherein G$^2$ is a reactive residue, such as a halogen atom, a methanesulfonyl group, etc. and R$^3$ is as defined in General Formula (I) above. In Formula 5 the symbol R$^{1'}$ may be as defined for R$^1$ in General Formula (I), or preferentially represents a suitably protected precursor of the residue R$^1$. As in Possibility A, deprotection is then required as a last step to generate the compounds of General Formula (I). Compounds of Formula 6 are either commercially available or can be prepared according to literature procedures (e.g. D. G. Crosby, R. V. Berthold; *J. Am. Chem. Soc.* 1960, 25, 1916; D. J. Brown, J. M. Lyall, *Aus. J. Chem.* 1964, 17, 803; L. A. Paquette, W. C. Farley, *J. Org. Chem.* 1967, 32, 2725; U.S. Pat. No. 4,233,294). Compounds of Formula 5 are prepared by reacting a compound of Formula 1 with ethylene glycol, or a suitably mono-protected precursor thereof, in the presence of a base such as potassium tert-butylate, NaH, in the presence or absence of an additional solvent such as 1,2-dimethoxyethane, DMSO, DMF, THF, etc at temperatures between rt and 110° C.

The synthetic pathway for the preparation of compounds of the General Formula (I) is further illustrated in Scheme 1 where the synthesis of Examples 1 and 2 of the present invention is compiled. Other examples can be prepared via the same synthetic pathway, adapting the substituents and reaction conditions.

The following numbering of compounds/derivatives refers exclusively to Scheme 1.

The 2-substituted malonic ester 2 was prepared by reacting methyl 4-bromophenylacetate 3 with dimethylcarbonate 4 in the presence of NaH in THF. The malonic ester derivative 2 was dissolved in methanol, sodium methylate was added, and stirring was continued for about 30 min followed by the addition of an formamidine hydrochloride 1. Stirring at ambient temperature was continued for another 8 h. After acidic work up, the 4,6-dihydroxypyrimidine 5 could be isolated in good to excellent yields. Compounds 5 or the tautomeric form thereof was transformed into the dichloro derivative 6 with phosphorus oxychloride in the presence of N,N-dimethylaniline at elevated temperatures (60-120° C.) in yields of 60 to 80%. The dichloride 6 was reacted with an excess of the sulfamide potassium salt 9 in DMSO at r.t. or 40 to 60° C. to give the monochloro-pyrimidine 10 in yields of 83 to 93% either after recrystallization or chromatography. The sulfamide building block 9 is prepared by reacting sulfamide (7) in the presence of 1 eq. of NaH with 3-benzyloxy-1-chloropropane in DMF at 50-60° C. followed by treatment with potassium tert-butylate. The pyrimidine derivatives 10 are then reacted with ethylene glycol in the presence of a base like potassium tert-butylate, sodium hydride or sodium at 80-110° C. for 16 to 48 h to give compound 11 in high yield. The alcohol 11 is then further transformed to compound 13 by reaction with 2-chloro-5-bromopyrimidine 12 in THF at either r.t. to approx. 60° C. in yields of 82-92%. Cleavage of the benzyl protecting group in 13 is effected by treatment with BBr$_3$ in dichloromethane. This affords the desired alcohol 14 in excellent yields (90%). The alcohol 14 is readily oxidised to the corresponding acid 15 upon treatment with Jones reagent in acetone.

Scheme 1: Exemplified synthesis of Examples 1 (14) and 2 (15).

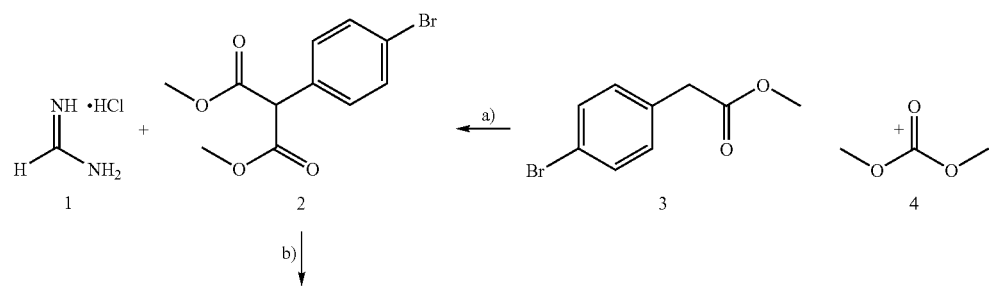

-continued
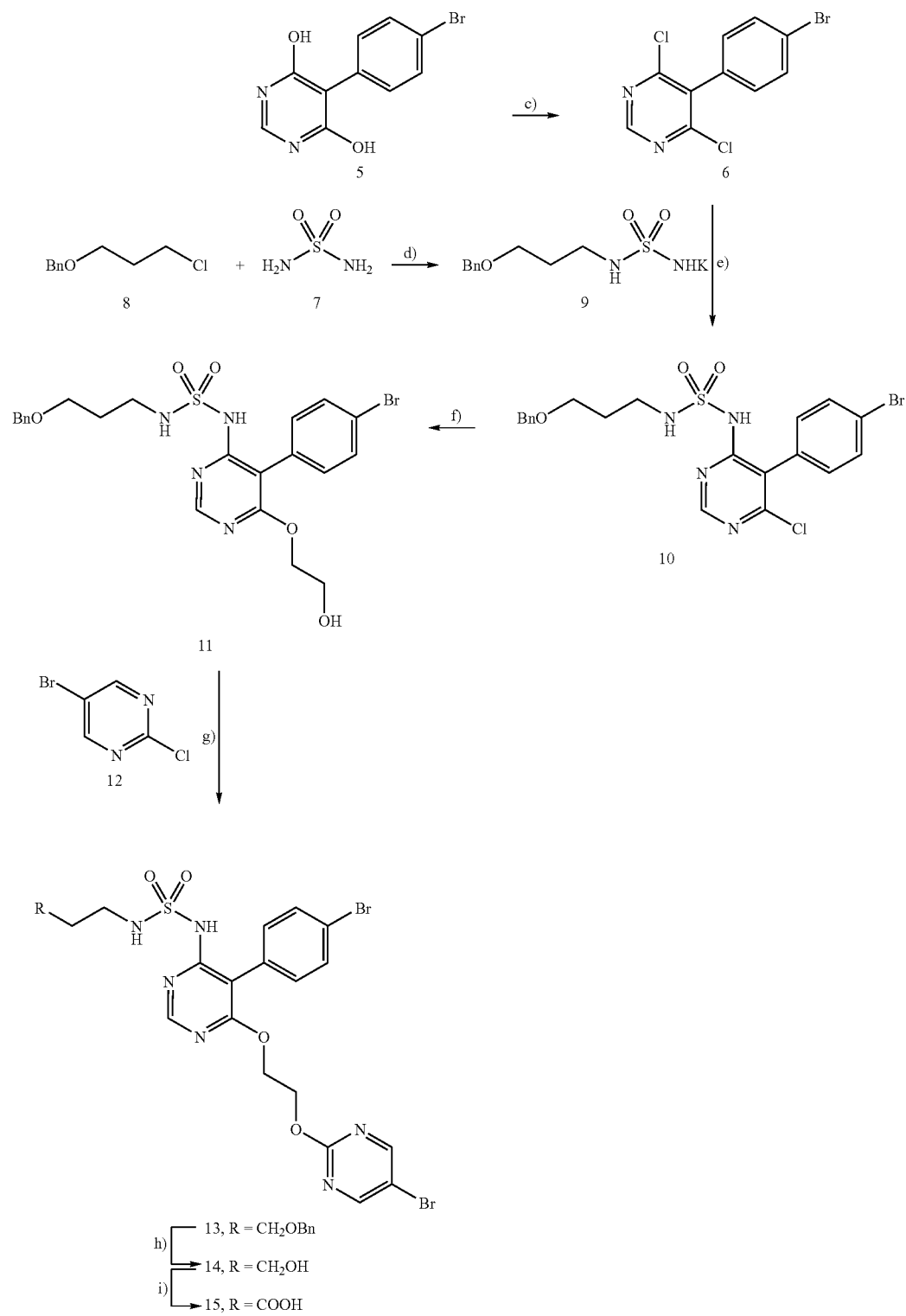
a) NaH, THF; rt b) NaOMe, MeOH, rt; c) POCl₃, N, N-dimethylaniline, 70-130° C.;
d) NaH, DMF, 50° C.; e) 9, DMSO, rt; f) K-tert.-butylate, ethylene glycol, 80-100° C;
g) NaH, THF, 10, 60° C.; h) BBr₃, DMC, 0° C. to rt; i) Jones reagent (CrO₃, H₂SO₄, H₂O), acetone, 0° C.

An alternative route to the sulfamide building blocks is depicted in Scheme 2 (M. J. Tozer, I. M. Buck et al.; *Bioorg. Med. Chem. Lett.,* 1999, 9, 3103. G. Dewynter et al.; *Tetrahedron,* 1993, 49, 65).

For further experimental descriptions see also EP 0 743 307 A1; EP 0 658 548 B1; EP 0 959 072 A1 (Tanabe Seiyaku); EP 0 633 259 B1; EP 0 526 708 A1; WO 96/19459 (F. Hoffmann-LaRoche); EP 0 882 719 A1 (Yamanouchi Pharmaceutical Co., Ltd); WO 02 53557 (Actelion Pharmaceuticals Ltd.).

Scheme 2: Alternative route to sulfamide building blocks.

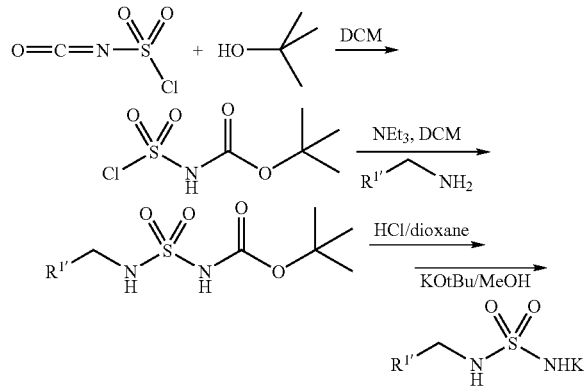

EXAMPLES

The following examples illustrate the invention. All temperatures are stated in ° C.

LIST OF ABBREVIATIONS

| | |
|---|---|
| Ac$_2$O | actetic anhydride |
| aq. | aqueous |
| CyHex | cyclohexane |
| DBU | 1,8-diazabicyclo[5.4.0]undec-7-en(1,5-5) |
| DCM | dichloromethane |
| DMAP | 4-dimethylaminopyridine |
| DMF | dimethylformamide |
| DMSO | dimethylsulfoxide |
| EA | ethyl acetate |
| Et$_3$N | triethylamine |
| Hex | hexane |
| HV | high vacuum conditions |
| KOtBu | potassium tert. butylate |
| MCPBA | m-chloroperbenzoic acid |
| min | minutes |
| rflx | reflux |
| rt | room temperature |
| THF | tetrahydrofuran |
| $t_R$ | retention time |

The following compounds were prepared according to the procedure described above and shown in Schemes 1 to 3. All compounds were characterized by 1H-NMR (300 MHz) and occasionally by $^{13}$C-NMR (75 MHz) (Varian Oxford, 300 MHz; chemical shifts are given in ppm relative to the solvent used; multiplicities: s=singlet, d=doublet, t=triplet; m=multiplet), by LC-MS[1] (Finnigan Navigator with HP 1100 Binary Pump and DAD, column: Zorbax SB-AQ 5 μm, 4.6× 50 mm, eluent: 5-95% acetonitrile in water (+0.04% TFA) in 1 min, 0.5 min 95% acetonitrile/5% water (+0.04% TFA), $t_R$ is given in min), by TLC (TLC-plates from Merck, Silica gel 60 F$_{254}$) and occasionally by melting point.

Example 1

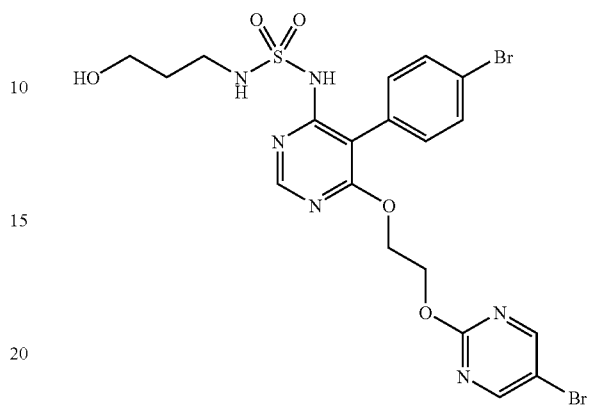

a) To a solution of 4-bromophenylacetic acid (50 g) in methanol (250 mL) thionyl chloride (34.2 mL) is added dropwise while the temperature of the reaction mixture is kept at 0-5° C. Upon complete addition, the cooling is removed and the mixture is allowed to warm to rt. Stirring is continued for 75 min before the solvent is removed in vacuo. The yellow oil is dissolved in benzene and evaporated. The residue is dissolved in EA, washed with water, brine, 2 N aq. Na$_2$CO$_3$, and brine. The organic phase is dried over MgSO$_4$ and evaporated and dried under high vacuum at 85° C. for 30 min to give 4-bromophenylacetic acid methyl ester (52.4 g) as a yellow oil. $^1$H-NMR(D$_6$-DMSO): 3.60 (s, 3H), 3.67 (s, 2H), 7.22 (d, 8.5, 2H), 7.50 (d, 8.5, 2H).

b) At 40° C. a solution of 4-bromophenylacetic acid methyl ester (52 g) in THF (100 mL) is carefully added over a period of 40 min to a suspension of NaH (15.6 g) in dry THF (450 mL). Stirring is continued for 70 min without heating and the temperature drops to 27° C. The evolution of gas has stopped before dimethylcarbonate (76.42 mL) is added dropwise while the temperature of the mixture is maintained at 29-31° C. Stirring is continued for 22 h at rt. The mixture is cooled to −10° C. and then carefully neutralized to pH 6-7 with aq. HCl before bulk of the THF is removed in vacuo. The residue is dissolved in EA (700 mL), washed three times with 1 N aq. HCl and once with brine, dried over MgSO$_4$. Most of the EA is evaporated before hexane is added. The product crystallizes over night at 4° C. The crystals are collected, washed with hexane and dried to give 2-(4-bromophenyl)-malonic acid dimethyl ester (45.9 g) as pale yellow crystals. $^1$H-NMR(D$_6$-DMSO): 3.66 (s, 6H), 5.07 (s, 1H), 7.30-7.34 (m, 2H), 7.55-7.59 (m, 2H).

c) A solution of 2-(4-bromophenyl)-malonic acid dimethyl ester (11.73 g) in methanol (100 mL) is added at 0° C. to a solution of sodium (2.83 g) in methanol (100 mL). The mixture is stirred for 18 h at rt before formamidine hydrochloride (4.10 g) is added. The suspension is stirred at rt for 4 h. The solvent is removed and the residue is suspended in 10% aq. citric acid (100 mL) and stirred for 10 min. The white precipitate is collected, washed with 10% aq. citric acid, water, evaporated three times from CyHex and dried under high vacuum at 40° C. to give 5-(4-bromophenyl)-pyrimidine-4,6-diol (9.90 g) as a pale beige powder. LC-MS: $t_R$=0.61 min, [M+H]$^+$=267.07; $^1$H-NMR(D$_6$-DMSO): 7.43-7.48 (m, 2H), 7.50-7.55 (m, 2H), 8.13 (s, 1H), 12.1 (s br, 2H).

d) To a suspension of 5-(4-bromophenyl)-pyrimidine-4,6-diol (9.90 g) in POCl$_3$ (130 mL) is carefully added N,N-dimethylaniline (13.5 mL). The mixture is heated to 130° C. for 2 h. The dark brown solution is evaporated and the residue is poured into ice/water. The suspension is diluted with 2 N HCl and water and stirred for 20 min. The precipitate is collected and washed with water. The solid material is dissolved in EA, washed with 1 N aq. HCl and brine. The organic phase is dried over MgSO$_4$ and evaporated. The material is further purified by column chromatography on silica gel eluting with hexane:EA 95:5 to 1:1 followed by crystallization from hexane/EA at −20° C. to give 4,6-dichloro-5-(4-bromophenyl)-pyrimidine (8.3 g) as pale yellow crystals. $^1$H-NMR(D$_6$-DMSO): 7.39-7.44 (m, 2H), 7.72-7.76 (m, 2H), 8.94 (s, 1H).

e) To a solution of sulfamide (1.0 g, 10.4 mmol) in dry DMF (50 mL) is added NaH (416 mg 60% dispersion in mineral oil, 10.4 mmol) in portions. After the evolution of gas has stopped, (3-bromo-propoxymethyl)-benzene (2.38 g, 10.4 mmol) is added and the reaction mixture is stirred at 50° C. for 18 h. The suspension is cooled to rt, neutralized with 1N aq. HCl (5 mL) and concentrated. The solid residue is suspended in acetone and filtered. The filtrate is evaporated and the residue is purified by column chromatography on silica gel eluting with hexane/EA to afford 3-benzyloxypropylsulfamide (651 mg) as a colourless oil. LC-MS: t$_R$=0.73 min, [M+H]$^+$=245.18; $^1$H NMR (CDCl$_3$): δ 7.39-7.27 (m, 5H), 4.94 (t br, J=4.6 Hz, 1H), 4.53 (s br, 2H), 4.50 (s, 2H), 3.60 (t, J=5.9 Hz, 2H), 3.26 (q, J=5.9 Hz, 2H), 1.89 (p, J=5.9 Hz, 2H).

The above 3-benzyloxypropylsulfamide is dissolved in methanol (25 mL) and treated with potassium tert. butylate (300 mg, 2.66 mmol). The solvent is removed in vacuo and the residue is dried under high vacuum to give 3-benzyloxypropylsulfamide potassium salt as a colourless solid.

f) A solution of 4,6-dichloro-5-(4-bromophenyl)-pyrimidine (405 mg, 1.33 mmol) and 3-benzyloxypropylsulfamide potassium (752 mg, 2.66 mmol) in DMSO is stirred at rt under argon for 18 h. The clear solution is poured onto 10% aq. citric acid solution (50 mL) and extracted twice with EA (2×75 mL). The organic extracts are washed with water (50 mL) and the solvent is evaporated. The residue is purified by column chromatography on silica gel eluting with hexane/EA 3:2 to afford 1-benzyloxypropanesulfamic acid [6-chloro-5-(4-bromophenyl)-pyrimidin-4-yl]-amide (524 mg) as a colourless foam. LC-MS: t$_R$=1.05 min, [M+H]$^+$=510.96; $^1$H NMR (CDCl$_3$): δ 8.44 (s, 1H), 7.71-7.65 (m, 2H), 7.40-7.28 (m, 5H), 7.18-7.12 (m, 2H), 6.90 (s, 1H), 6.05 (t, J=5.9 Hz, 1H), 4.49 (s, 2H), 3.57 (t, J 0 5.9 Hz, 2H), 3.18 (q, J=5.9 Hz, 2H), 1.88 (p, J=5.9 Hz, 2H).

g) To as suspension of 1-benzyloxypropanesulfamic acid [6-chloro-5-(4-bromophenyl)-pyrimidin-4-yl]-amide (524 mg, 1.02 mmol) in ethylene glycol (10 mL) is added potassium tert. butylate (1.15 g, 10.2 mmol). The resulting clear solution is stirred at 85-90° C. for 48 h before it is cooled to rt, diluted with 10% aq. citric acid solution (75 mL) and extracted with EA (2×75 mL). The organic extracts are washed with water (2×75 mL) and the solvent is removed in vacuo. The remaining residue is purified by column chromatography on silica gel eluting with heptane/EA 1:1 to give 1-benzyloxypropanesulfamic acid[6-(2-hydroxyethoxy)-5-(4-bromophenyl)-pyrimidin-4-yl]-amide (517 mg) as a colourless foam. LC-MS: t$_R$=0.97 min, [M+H]$^+$=536.99; $^1$H NMR (CDCl$_3$): δ 8.34 (s, 1H), 7.65-7.60 (m, 2H), 7.38-7.29 (m, 5H), 7.20-7.15 (m, 2H), 6.86 (s br, 1H), 5.98 (t br, J=5.9 Hz, 1H), 4.51-4.45 (m, 4H), 3.86-3.82 (m, 2H), 3.56 (t, J=5.9 Hz, 2H), 3.17 (q, J=6.4 Hz, 2H), 2.54 (s br, 1H), 1.93-1.84 (m, 2H).

h) To a solution of 1-benzyloxypropanesulfamic acid[6-(2-hydroxyethoxy)-5-(4-bromophenyl)-pyrimidin-4-yl]-amide (237 mg, 0.441 mmol) in THF (10 mL) is added NaH (58 mg, 60% dispersion in mineral oil, 1.32 mmol). The mixture is stirred for 5 min before 2-chloro-5-bromopyrimidine (128 mg, 0.662 mmol) is added. The reaction mixture is stirred at 60° C. for 2 h, diluted with 10% aq. citric acid solution (75 mL) and extracted with EA (75 mL). The organic extract is washed twice with water (2×50 mL) and concentrated. The remaining residue is purified on prep. tlc plates (silica gel, heptane/EA 1:1) to afford 1-benzyloxypropanesulfamic acid [6-(2-(5-bromopyrimid-2-yloxy)-ethoxy)-5-(4-bromophenyl)-pyrimidin-4-yl]-amide (283 mg) as a colourless foam. LC-MS: t$_R$=1.09 min, [M+H]$^+$=693.12; $^1$H NMR (CDCl$_3$): δ 8.48 (s, 2H), 8.34 (s, 1H), 7.58-7.53 (m, 2H), 7.38-7.28 (m, 5H), 7.16-7.11 (m, 2H), 6.84 (s, 1H), 5.97 (t, J=5.9 Hz, 1H), 4.73-4.68 (m, 2H), 4.64-4.60 (m, 2H), 4.50 (s, 2H), 3.56 (t, J=5.9 Hz, 2H), 3.17 (q, J=6.4 Hz, 2H), 1.88 (p, J=5.9 Hz, 2H).

i) A solution of 1-benzyloxypropanesulfamic acid[6-(2-(5-bromopyrimid-2-yloxy)-ethoxy)-5-(4-bromophenyl)-pyrimidin-4-yl]-amide (283 mg, 0.408 mmol) in DCM (15 mL) is cooled to −78° C. an then slowly treated with BBr$_3$ (0.816 mL of a 1 M solution in DCM). The reaction mixture is allowed to warm to rt and stirring is continued for 1 h. Methanol (approx. 10 mL) is added to the suspension and stirring is continued for another 10 min before the mixture is diluted with 10% aq. citric acid solution (75 mL) and extracted with DCM (2×75 mL). The organic extracts are washed with water (50 mL), dried over MgSO$_4$, filtered and concentrated. The crude product is purified on prep. tlc plates (silica gel, DCM with 10% methanol) to afford 1-hydroxypropanesulfamic acid[6-(2-(5-bromopyrimid-2-yloxy)-ethoxy)-5-(4-bromophenyl)-pyrimidin-4-yl]-amide (223 mg) as a pale grey foam. LC-MS: t$_R$=0.92 min, [M+H]$^+$=602.87; $^1$H NMR (CDCl$_3$): δ 8.48 (s, 2H), 8.44 (s, 1H), 7.58-7.54 (m, 2H), 7.18-7.13 (m, 2H), 6.91 (s, 1H), 5.93 (t, J=6.4 Hz, 2H), 4.75-4.70 (m, 2H), 4.65-4.60 (m, 2H), 3.75 (t, J=5.2 Hz, 2H), 3.17 (q, J=6.4 Hz, 2H), 1.85-1.76 (m, 3H).

Example 2

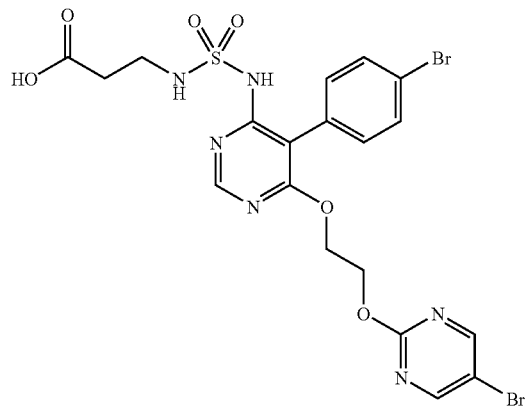

To a solution of 1-hydroxypropanesulfamic acid[6-(2-(5-bromopyrimid-2-yloxy)-ethoxy)-5-(4-bromophenyl)-pyrimidin-4-yl]-amide (110 mg, 0.183 mmol) in acetone (3 mL) is Jones' reagent (96 μL, prepared from 6.7 g CrO$_3$, 12 mL H$_2$O and 5.8 mL H$_2$SO$_4$) at 0° C. The orange to brown solution is stirred at 0° C. for 15 min. The reaction mixture becomes darker and dark green sticky precipitate forms. The mixture is carefully filtered over cotton wool and purified by chromatography on tlc plates (silica gel, DCM containing 10% methanol) to furnish 1-hydroxycarbonylethanesulfamic acid[6-(2-(5-bromopyrimid-2-yloxy)-ethoxy)-5-(4-bromophenyl)-pyrimidin-4-yl]-amide (93 mg) as a beige foam. LC-MS: $t_R$=0.92 min, [M+H]$^+$=616.88; $^1$H NMR (CDCl$_3$): δ 8.58 (s, 2H), 8.06 (s, 1H), 7.62-7.58 (m, 2H), 7.23-7.18 (m, 2H), 6.29 (s br, 1H), 4.82-4.77 (m, 2H), 4.68-4.63 (m, 2H), 3.45-3.38 (m, 2H), 2.55-2.48 (m, 2H).

The invention claimed is:
1. A compound of Formula (I):

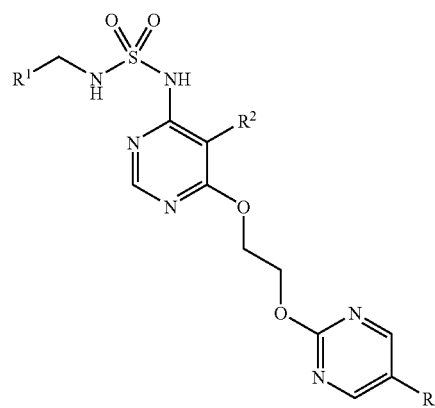

Formula (I)

wherein
R$^1$ represents —CH(OH)—CH$_3$, —CH$_2$—CH$_2$OH, —CH$_2$COOH, —CH$_2$—CH$_2$—CH$_2$OH, or —CH$_2$—CH$_2$—COOH;
R$^2$ represents 4-bromophenyl, 4-chlorophenyl, 4-methylphenyl, 2-methoxyphenoxy, 3-methoxyphenoxy, or 2-chloro-5-methoxy-phenoxy; and
R$^3$ represents bromine or chlorine, or an optically pure enantiomer, a mixture of enantiomers, or a pharmaceutically acceptable salt thereof.

2. The compound of claim 1, wherein R$^1$ represents —CH$_2$—CH$_2$OH.

3. The compound of claim 1, wherein R$^1$ represents —CH$_2$—COOH.

4. The compound of claim 1, wherein R$^2$ represents 4-bromophenyl.

5. The compound of claim 1, wherein R$^3$ represents bromine.

6. The compound of claim 1, wherein R$^1$ represents —CH$_2$—CH$_2$OH or —CH$_2$—COOH, and R$^2$ represents 4-bromophenyl or 4-chlorophenyl.

7. The compound of claim 1, wherein R$^1$ represents —CH$_2$—CH$_2$OH and R$^2$ represents 4-bromophenyl.

8. The compound of claim 1, wherein R$^1$ represents —CH$_2$—COOH and R$^2$ represents 4-bromophenyl.

9. A compound selected from the group consisting of
3-hydroxypropylsulfamic acid {5-(4-bromophenyl)-6-[2-(5-bromoprimidin-2-yloxy)-ethoxy]-pyrimidin-4-yl}-amide, and
2-hydroxycarbonylethylsulfamic acid{5-(4-bromophenyl)-6-[2-(5-bromopyrimidin-2-yloxy)-ethoxy]-pyrimidin-4-yl}-amide.

10. A pharmaceutical composition containing at least one compound of claim 1 as an active ingredient and a pharmaceutically acceptable excipient.

11. A process for the manufacture of the pharmaceutical composition of claim 10, wherein the process comprises mixing one or more active ingredients with the pharmaceutically acceptable excipient.

12. A pharmaceutical composition containing at least one compound of claim 9 as an active ingredient and a pharmaceutically acceptable excipient.

13. A process for the manufacture of the pharmaceutical composition of claim 12, wherein the process comprises mixing one or more active ingredients with the pharmaceutically acceptable excipient.

* * * * *